United States Patent [19]
Heiliger et al.

[11] Patent Number: 5,213,578
[45] Date of Patent: May 25, 1993

[54] ANESTHESIA SET

[75] Inventors: Raymund Heiliger, Herzogenrath; Joachim Gross, Sindelfingen, both of Fed. Rep. of Germany

[73] Assignee: Vygon GmbH & Co. KG, Aachen, Fed. Rep. of Germany

[21] Appl. No.: 934,926

[22] Filed: Aug. 25, 1992

[30] Foreign Application Priority Data

Aug. 28, 1991 [DE] Fed. Rep. of Germany ....... 4128530

[51] Int. Cl.$^5$ ............................................. A61M 5/178
[52] U.S. Cl. .................... 604/158; 604/164; 604/274
[58] Field of Search ............... 604/158-170, 604/272, 274

[56] References Cited

U.S. PATENT DOCUMENTS

| | | | |
|---|---|---|---|
| 2,748,769 | 6/1956 | Huber | 604/274 |
| 2,922,420 | 1/1960 | Cheng | 604/158 |
| 4,958,901 | 9/1990 | Coombs | 604/158 |
| 5,100,390 | 3/1992 | Lubeck et al. | 604/158 |
| 5,106,376 | 4/1992 | Mononen et al. | 604/164 |
| 5,163,901 | 11/1992 | Eldor | 604/158 |
| 5,167,645 | 12/1992 | Castillo | 604/158 |

Primary Examiner—John D. Yasko
Assistant Examiner—Anthony Gutowski
Attorney, Agent, or Firm—Mark T. Basseches

[57] ABSTRACT

To securely introduce the distal tip of a spinal cannula through an epidural cannula into a spinal canal, a mandrel is placed in the epidural cannula. The mandrel is provided with a recess or guideway extending over its length. The guideway is aligned with an axial opening in the epidural cannula, so that the spinal cannula, when pushed forward through the recess, is guided positively to the axial opening and can pass through it unhindered, in order to get into the spinal canal. The mandrel includes a radially offset distal portion which enters and seals a curved, offset portion of the epidural cannula to avoid coring of tissue and to snap fittedly connect the mandrel and epidural cannula.

4 Claims, 1 Drawing Sheet

FIG. 1
FIG. 2
FIG. 3
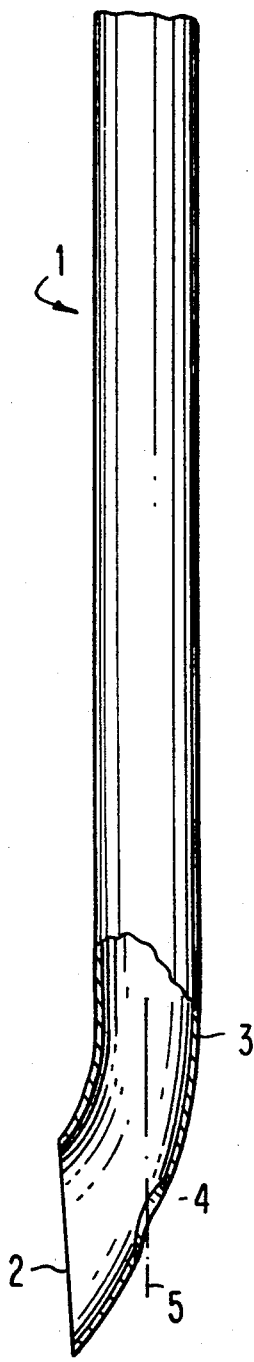
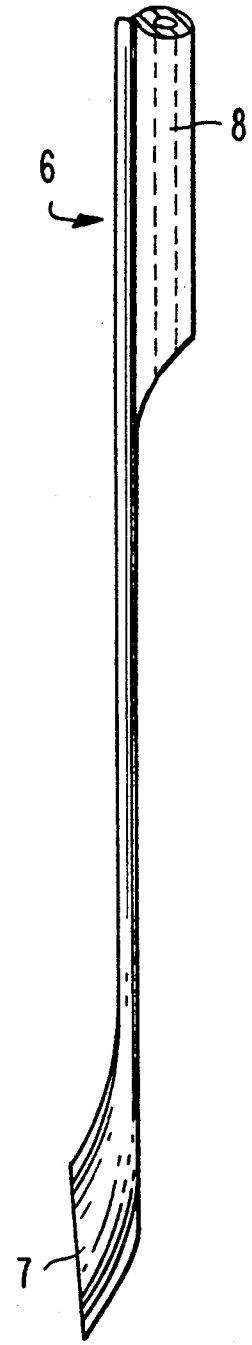
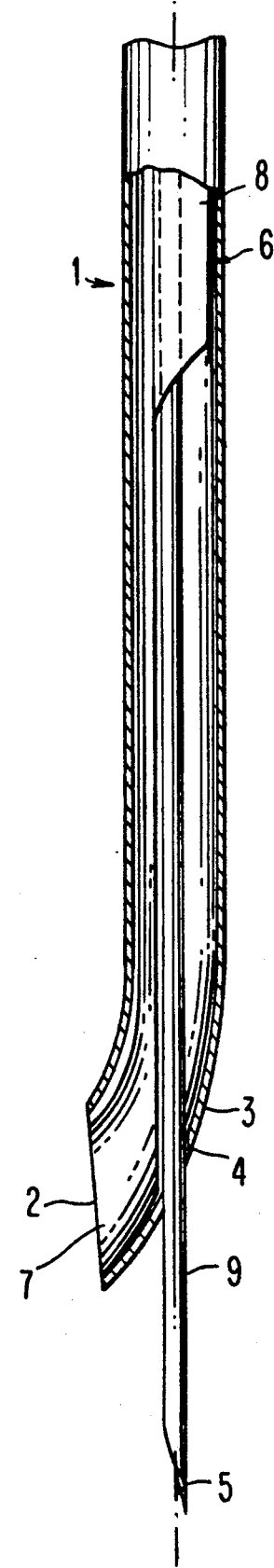

ANESTHESIA SET

BACKGROUND OF THE INVENTION

The invention relates to an anesthesia set for the receipt of an epidural catheter. The set includes an epidural cannula, and a spinal cannula. The epidural cannula, containing the mandrel, is provided at its distal end with a radial outlet opening for the epidural catheter and with an axial outlet opening for the spinal cannula.

Such an anesthesia set, known from DE 39 22 406 C1, consists of a substantially straight epidural cannula with an outlet opening, a spinal cannula which is longer and thinner than the epidural cannula and is insertable therein in such a way that it protrudes by its distal end from the epidural cannula, and an epidural catheter that can be pushed through the epidural cannula. The tip of the epidural cannula is bent, and the passage opening for the epidural catheter is oriented radially sideways. In the outer wall of the curvature of the tip, an outlet opening for the spinal cannula centered on the longitudinal center line of the epidural cannula is provided. This outlet opening is smaller than the outside diameter of the epidural catheter.

Handling of the known anesthesia set is easy for the user only if the tip of the spinal cannula positively enters the spinal canal in a straight line and if the epidural catheter can positively be introduced into the epidural space. While such introduction of the epidural catheter presents no problem in principle, special precautions are required—as the spinal cannula is much thinner than the epidural cannula—for the proper insertion of the tip of the spinal cannula into the spinal canal, so that especially the tip of the spinal cannula will not miss the axial outlet opening in the epidural cannula.

It has been proposed, therefore, for the known anesthesia set to attach on the spinal cannula, in spaced relation to its tip, a coaxial guide ring whose outside diameter is slightly smaller than the inside diameter of the epidural cannula. Because such a guide ring is obviously unable to prevent an oblique position of the spinal cannula inside the epidural cannula, it is recommended, for improving the guidance, to form the guide ring as a circumferentially closed circular-cylindrical tube, preferably consisting of a plastic hose which is to extend over the full length of the spinal cannula, leaving free a cannula section near the tip. The secure guiding and positioning of the spinal cannula thus requires considerable additional expenditure, by which the cost of manufacture of the known anesthesia set is increased.

SUMMARY OF THE INVENTION

It is the object of the invention to design an anesthesia set of the initially described kind in such a way that it is easier to handle and that with it the spinal cannula can be guided and positioned just as securely as the epidural catheter, without the necessity of providing the spinal cannula with an auxiliary means or adapting it to the larger inside diameter of the epidural cannula in some other way.

For the solution of this problem there is provided an anesthesia set for receiving the epidural catheter comprised of an epidural cannula having an axial bore and a curved distal end. A radial opening for the catheter is formed in the curved end, which end is also formed with an axial opening for receipt of the distal end of a spinal cannula. A mandrel is provided having at its proximal end a tubular portion intimately fitted within the bore of the epidural cannula, the tubular portion including a bore coaxial with the bore of the epidural cannula. A flexible recessed neck portion forming with the coaxial bore a continuing guideway, extends from the tubular portion of the mandrel to a radially offset distal end.

When the mandrel is inserted into the epidural cannula the distal end is deflected into the curved end of the epidural cannula to snap fittedly connect these parts. When thus connected the mandrel provides a guideway for reliably guiding the distal end of a spinal cannula, inserted through the bore of the mandrel into the axial opening in the distal end of the epidural cannula.

This also facilitates the handling of the anesthesia set, because the distal end of the mandrel fills the radial lumen of the epidural cannula to avoid punching out or coring of tissue and can stay in the epidural cannula during the introduction of the spinal cannula and during the performance of the spinal anesthesia; it needs to be removed from the epidural cannula only just before the epidural catheter is inserted.

According to a variant of the invention, the recess is produced by a bore or slot coaxial with the longitudinal axis of the mandrel.

Since the axial outlet opening for the spinal cannula is centered on the longitudinal center line of the epidural cannula, the bore coaxial with the longitudinal axis of the mandrel is positively aligned with the axial outlet opening, so that, a surface of the recess is aligned with a projection of a boundary of the outlet opening, whereby the soffit of the recess merges with the soffit of the axial passage opening in a continuous manner.

In order to bring the tip of the spinal cannula to the axial outlet opening in the epidural cannula in a controlled manner, it may, according to another variant of the invention, be sufficient to produce the recess in the mandrel by a groove parallel to its longitudinal axis.

The lateral aperture cross-section of the groove in the distal end of the mandrel is closed off by the curved wall of the epidural cannula, so that a guide channel for the spinal cannula is created by means of the groove, through which the tip of the spinal cannula is positively guided toward the outlet opening in the epidural cannula.

Lastly, a variant of the invention further provides that the recess is formed by a cross-section reduction of the mandrel over a partial length between the axial outlet opening of the epidural cannula in the direction of the proximal end.

Due to the enlarged recess, even in the presence of the mandrel and the spinal cannula, there remains inside the epidural cannula a free cavity which facilitates the detection of a pressure loss during the spinal anesthesia, as this cavity offers a much lower resistance to the analgesic than does the dura-sheathed content in the spinal canal.

BRIEF DESCRIPTION OF THE DRAWINGS

The drawings represent as an example of realization of the anesthesia set according to the invention in each instance a side view, partly in section, of a distal end piece.

FIG. 1 shows an epidural cannula.
FIG. 2 shows a mandrel.
FIG. 3 depicts the epidural cannula with the mandrel and a spinal cannula in the inserted state.

DESCRIPTION OF PREFERRED EMBODIMENT

An epidural cannula 1, consisting in known manner of a straight piece of tube, is bent at its distal end. By a grinding parallel to its longitudinal center line, the epidural cannula 1 is provided with a radial outlet opening 2. In the curvature zone a concave wall portion 3 of the epidural cannula 1 is provided with an axial outlet opening 4, which is centered on the dash-dot longitudinal center line 5 of the epidural cannula 1.

As it is necessary to pierce the skin and muscle tissue with the tip of the epidural cannula a mandrel 6 is inserted into the epidural cannula to prevent the punching out of skin and tissue parts, the mandrel forming with a distal end piece 7 a flush closure for the radial outlet opening 2 of the epidural cannula 1.

The mandrel 6 is provided with a recess 8 in the form of a bore coaxial with its longitudinal axis, the cross-section of the bore corresponding to the projection plane of the axial outlet opening 4 in the epidural cannula, and the bore as well as the latter being centered on the longitudinal center line of the epidural cannula 1. Over a partial length of the mandrel 6, the mandrel is cut away between the axial outlet opening 4 in the direction toward the proximal end, whereby the mandrel 6 is flattened over one half of its cross-section. The thinned neck portions interposed between distal end 7 and the proximal end of the mandrel is flexible and thus, upon insertion of the mandrel into the cannula 1, the distal end snaps radially into the curved portion of cannula 1 releasably locking the mandrel in the position illustrated in FIG. 3.

As FIG. 3 illustrates, the mandrel 6 placed in the epidural cannula 1 serves not only to close the radial outlet opening 2, but moreover to guide a spinal cannula 9 through the epidural cannula 1 and through the axial outlet opening 4 thereof. The recess 8, adapted to the spinal cannula 9, and having the form of an axial bore in the mandrel 6, its diameter being only slightly greater than the outside diameter of the proximal end of the spinal cannula 9, guarantees a secure guidance of the spinal cannula 9 through the axial passage opening 4 in the epidural cannula 1.

As will be apparent to those skilled in the art and familiarized with the instant disclosure, numerous variations in details of construction will occur within the spirit of the instant invention. Accordingly, the invention is to be broadly construed within the scope of the claims.

Having thus described the invention and illustrated its use, what is claimed as new and is desired to be secured by Letters Patent is:

1. An anesthesia set for the receipt of an epidural catheter comprising an elongate epidural cannula having an axial bore leading to a curved distal end, a radially directed outlet at said distal end of said epidural cannula for the receipt of said epidural catheter, an axial outlet formed in said distal end of said epidural cannula in alignment with the axis of said bore, a mandrel insertable into said bore and including a distal end adapted to seal said radial outlet in the inserted position of said mandrel within said epidural cannula, said mandrel including a guideway in axial alignment with said bore, and a spinal cannula including an external diameter portion complementally sized to said guideway, whereby said distal end of said spinal cannula is guided by said mandrel through said axial outlet responsive to insertion of said spinal cannula into said epidural cannula.

2. Anesthesia set according to claim 1, wherein said guideway comprises a bore in said mandrel coaxial with the longitudinal axis of the mandrel.

3. Anesthesia set according to claim 1, wherein said guideway comprises a groove in said mandrel parallel to the longitudinal axis of the mandrel.

4. Anesthesia set in accordance with claim 1 wherein said mandrel includes a hollow tubular portion at the proximal end thereof, the exterior of said tubular portion being sized to be intimately received within said bore of said epidural cannula, said tubular portion including a bore coaxial with the axis of said epidural cannula, said mandrel including a recessed flexible neck portion interposed between said distal end thereof and said tubular portion, said distal end of said mandrel in the inserted position of said mandrel into said epidural catheter being deflected radially into said curved end of said epidural catheter to thereby snap fittedly connect said mandrel and epidural catheter.

* * * * *